(12) United States Patent
Bartels-Arntz et al.

(10) Patent No.: US 7,582,601 B2
(45) Date of Patent: Sep. 1, 2009

(54) USE OF TRYPTOPHAN RICH PEPTIDES

(75) Inventors: Marjoleine Maria Theodora Gerarda Bartels-Arntz, Terheijden (NL); Johannes Maria Josef Margaretha Steijns, Boekel (NL); Petronella Wilhelmina Josephina Rosa Caessens, Wageningen (NL)

(73) Assignee: Campina B.V., Zaltbommel (NL)

( * ) Notice: Subject to any disclaimer, the term of this patent is extended or adjusted under 35 U.S.C. 154(b) by 48 days.

(21) Appl. No.: 10/544,862

(22) PCT Filed: Feb. 7, 2003

(86) PCT No.: PCT/NL03/00084

§ 371 (c)(1),
(2), (4) Date: May 2, 2006

(87) PCT Pub. No.: WO2004/069265

PCT Pub. Date: Aug. 19, 2004

(65) Prior Publication Data

US 2006/0257497 A1    Nov. 16, 2006

(51) Int. Cl.
 *A61K 35/20*    (2006.01)
(52) U.S. Cl. .......................... 514/2; 424/535
(58) Field of Classification Search ............... None
 See application file for complete search history.

(56) References Cited

U.S. PATENT DOCUMENTS

| 6,429,190 | B1 | 8/2002 | Portman | |
|---|---|---|---|---|
| 2002/0119915 | A1 | 8/2002 | Portman | |
| 2002/0119948 | A1 | 8/2002 | Portman | |
| 2004/0058866 | A1* | 3/2004 | Mallee et al. | 514/12 |

FOREIGN PATENT DOCUMENTS

| WO | WO 87/01590 | 3/1987 |
|---|---|---|
| WO | WO 99/52363 | 10/1999 |
| WO | WO 02/46210 | * 6/2002 |
| WO | WO 02/46210 A1 | 6/2002 |

OTHER PUBLICATIONS

Aoyama et al., Biosci. Biotechno;. Biochem. 2000, vol. 64 (12) pp. 2594-2600.*
Backus et al., Regulatory peptides, 1995, vol. 57, pp. 123-131.*
Backus et al., "Elevation of Plasma Cholecystokinin (CCK) Immunoreactivity by Fat, Protein, and Amino Acids in the Cat, A Carnivore," Regulatory Peptides, 1995, p. 123-131, vol. 57.
Bray, "Reciprocal Relation of Food Intake and Sympathetic Activity: Experimental Observations and Clinical Implications," International Journal of Obesity, 2000, p. S8-S17, vol. 24, Suppl. 2.
Aoyama et al., "Effect of Soy and Milk Whey Protein Isolates and Their Hydrolysates on Weight Reduction in Genetically Obese Mice," Biosci. Biotechnol. Biochem., 2000, p. 2594-2600, vol. 64 (12).
Maher et al., "The Serotoin Precursor 5-Hydroxy-LTryptophan Decreases Food Intake in Food-Deprived and Stressed Rats," XP-002257148, Mar. 7, 2001, Abstract.
Nagaoka, et al., "Comparative Studies on the Serum Cholesterol Lowering Action of Whey Protein and Soybean Protein in Rats," Biosci. Biotech. Biochem, 1992, Vol. 56, pp. 1484-1485.
Nagaoka, et al., "Effects of Whey Protein and Casein on the Plasma and Liver Lipids in Rats," Agric. Biol. Chem, 1991, Vol. 55, No. 3, pp. 813-818.
Huerou-Luron, et al., "Source of Dietary Protein Influences Kinetics of Plasma Gut Regulatory Peptide Concentration in Response to Feeding in Preruminant Calves," Comp. Biochem. Physiol., 1998, Vol. 119A, No. 3, pp. 817-824.
Official Action from corresponding Japanese Patent Application No. 2004-567923, Apr. 7, 2009, English translation.

* cited by examiner

*Primary Examiner*—Christopher R. Tate
*Assistant Examiner*—Roy Teller
(74) *Attorney, Agent, or Firm*—Gilberto M. Villacorta; Sunit Talapatra; Foley & Lardner LLP

(57) ABSTRACT

The novel use of peptides derived from whey protein hydrolysate as active ingredient in a medicament or as food ingredient for elevating the cholescystokinin level in the blood, and for preventing or treatment of overweight and/or obesity, in an animal, including human, in need thereof.

15 Claims, 1 Drawing Sheet

USE OF TRYPTOPHAN RICH PEPTIDES

BACKGROUND OF THE INVENTION

1. Field of the Invention

The invention relates to a novel use of peptides derived from a whey protein hydrolysate.

2. Description of the Related Art

In the art, several attempts have been made to elevate the cholecystokinin (CCK) levels in the intestine, e.g. by providing specially designed nutritive agents that are said to stimulate the release of CCK. Such a nutritive agent is described in US patent application US2002/0119915, wherein a powder composition is disclosed, comprising proteins, fatty acids and a proteinase inhibitor, that is to be ingested before a meal to extend post meal satiety. The proteinase inhibitor was described to be critical for the stimulation of CCK release. Although whey protein could be used as protein source in the said composition, peptides derived from a whey protein hydrolysate were not disclosed. Moreover, the presence of a proteinase inhibitor would prevent the formation of a hydrolysate.

It has now been surprisingly found that peptides derived from a whey protein hydrolysate have a positive effect in elevating the CCK level in an animal, including humans, in particular in the blood. CCK is known to play an important role in the treatment and prevention of obesity and overweight, by mediating a satiety signal in the animal (see e.g. A. Stafleu, Leads in Life Sciences, 2002, (14) pp. 9-10).

SUMMARY OF THE INVENTION

Therefore, the invention provides a novel use of peptides, derived from a whey protein hydrolysate, as active ingredient in a medicament or as food ingredient for elevating the cholecystokinin level in the blood of an animal, including human, in need thereof, and also for preventing or treatment of overweight and/or obesity.

The term "peptides" is known in the art; herein the term relates to amino acid chains, preferably having a molecular weight of 500-5000 Dalton, more preferably between 1000-3000 Dalton. It is e.g. general knowledge that proteins can be fragmented by hydrolysis into peptides that consist of a small number of amino acids.

The peptides for use according to the present invention are obtained by hydrolysis of whey protein, more preferably by enzymatic cleavage of a whey protein. Hydrolysis and enzymatic cleavage of proteins to obtain peptides, i.e. protein fragments, are known techniques in the art.

DETAILED DESCRIPTION OF THE INVENTION

In a preferred embodiment, the peptides are prepared by cleaving the whey protein by one or more acid proteases or cysteine proteases, preferably chosen from the group, consisting of pepsin, papain or bromelain, or a mixture of two or more thereof. Preferably, the protein source is cleaved by pepsin, preferably at a pH of between 1,5-3,5, more preferably between 2-3.

The peptides are derived from whey protein. It is observed that whey proteins have a relatively high tryptophan content (about 1,8 w/w %). In a very attractive embodiment of the invention, the peptides are derived from whey protein isolate, preferably whey protein concentrate, most preferably from α-lactalbumin enriched whey protein concentrate (WPC) or α-lactalbumin enriched whey protein isolate (WPI). The terms "whey protein isolates" and "whey protein concentrates" are known in the field, see e.g. Walstra et al., 1999, Dairy Technology, ISBN 0-8247-0228-X. Whey protein concentrate is a whey protein product having 35-80 w/w % protein, whereas whey protein isolate has a protein content of 90 w/w % or higher. An example of WPC is Lacprodan 80 from ARLA, Denmark; an example of WPI is Bipro from Bio-isolates Ltd. α Lactalbumin enriched whey protein isolates and concentrates are derived from whey protein and have an elevated α-lactalbumin content. The α-lactalbumin content of αWPC may e.g. vary, depending on the preparation, between 20-80 w/w %, whereas the alactalbumin content of normal WPC is about 12-18 w/w %. α-Lactalbumin has a high tryptophan content of about 5,8w/w %. A whey protein isolate containing about 60w/w % α-lactalbumin can be obtained from DMV International, the Netherlands, and is described in EP 0 604 684.

In a preferred use according to the invention, the peptides are obtained by an isolation method, the said isolation comprising the steps of:

a) providing an aqueous whey protein hydrolysate, b) controlling the pH of the aequeous whey protein hydrolysate to 4,0-6,0, forming a peptide precipitate, and c) isolation of the precipitated peptides.

As outlined above, the skilled person is aware of suitable conditions for performing hydrolysis reactions on the whey protein. The term "controlling" of the pH means that the pH should be adjusted or kept at the above described pH value during the precipitation of the peptides.

Isolation of the precipitated peptides can be done by methods that are known in the art. The precipitated peptides can e.g. be collected by centrifugation, decantation or filtration and the like. In order to obtain a long shelf life, the isolation preferably comprises a drying step. The skilled person is aware of suitable drying techniques. As will be shown in the examples it has been found that the precipitated peptides, are effective in elevating the CCK level and can be used against overweight and obesity.

Preferably, the precipitation is carried out at a temperature below 20° C. Below said temperature, the peptides have shown to precipitate very efficiently.

As outlined above, the aqueous peptide mixture, i.e. the whey protein hydrolysate is preferably prepared by enzymatic cleavage of whey protein, and more preferably, the whey protein is cleaved at acidic pH by one or more acid proteases or cysteine proteases, especially by one or more enzymes, chosen from the group, consisting of pepsine, rennin, acid fungal proteases, chymosin, papain, bromelain, chymopapain or ficin or mixtures of two or more thereof. By cleavage of whey protein by one or more of said acid proteases, especially pepsin at a pH between 1,5 and 3,5, preferably between 2-3, peptides having a hydrophobic nature are generated. It was found that from these peptide mixtures, the effective peptides could very efficiently be selectively isolated by controlling the pH to 4,0-6,0, preferably to around 5,0. In case the pH at the enzymatic cleavage was below 4,0, the pH was to be adjusted to 4,0-6,0 in order to precipitate the peptides. Preferably, the enzymatic activity is quenched by inactivation of the enzyme before the precipitation step. The skilled person will know how to inactivate the proteolytic enzyme. In case an enzyme is chosen having its pH optimum within the above mentioned pH range of 4,5-6,0, such as e.g. papaine or bromelaine, it will be possible to design the isolation method in such way that cleavage of the whey protein and precipitation of the peptides can occur simultaneously. Care has to be taken that the precipitation is done at conditions wherein the hydrolysed peptides preferentially precipitate; otherwise, a precipitate of partial hydrolysed peptides may be obtained.

Preferably, the peptide mixture is desalted before the step of controlling the pH (step b). It has been found that a desalting step prior to the pH controlling step leads to an improved yield of precipitated peptides. Desalting is a known technique and can be done by e.g. nanofiltration, ultrafiltration or electrodialysis. Especially when the peptides are obtained by enzymatic cleavage, desalting the obtained peptide mixture leads to improved yields. Desalting is preferably carried out such that 50-95% of the salt present during the cleavage reaction is removed from the peptide mixture.

By the above-described isolation method, a peptide mixture can be obtained, that can advantageously be used in e.g. a food ingredient or a medicament for the elevation of CCK levels and against obesity and overweight.

The invention further relates to a method for elevating the cholecystokinin level in the blood of an animal, including human, in need thereof, comprising the step of administering to the animal an effective amount of peptides from a whey protein hydrolysate as described above. The administration can be performed according to methods, known in the art; the peptide mixture can be administered as a medicament, comprising a suitable carrier. The administration route can be any route known in the art, such as, but not limited to oral percutaneous route. The medicament can be in any known form, such in the form of pills, ointments, or injection fluids. The peptide mixture can also be administered as a powder or be incorporated in a food product.

The invention also relates to a method for preventing or treatment of overweight and/or obesity of an animal, including human, in need thereof, comprising the step of administering to the animal an effective amount of peptides from a whey protein hydrolysate as described above.

BRIEF DESCRIPTION OF THE DRAWING

The invention will now be further illustrated by some non-limiting examples and a figure, wherein the mean CCK concentrations in plasma of human volunteers (in pmol/l, n=8) is shown at several time points after consumption of peptides according to the invention (black squares), of amino acids including tryptophan (blank diamonds), of tryptophan as amino acid (black triangle) and of a reference substance (cross).

The percentages in the examples are weight percentages, unless indicated otherwise.

EXAMPLE 1

Figure 1:
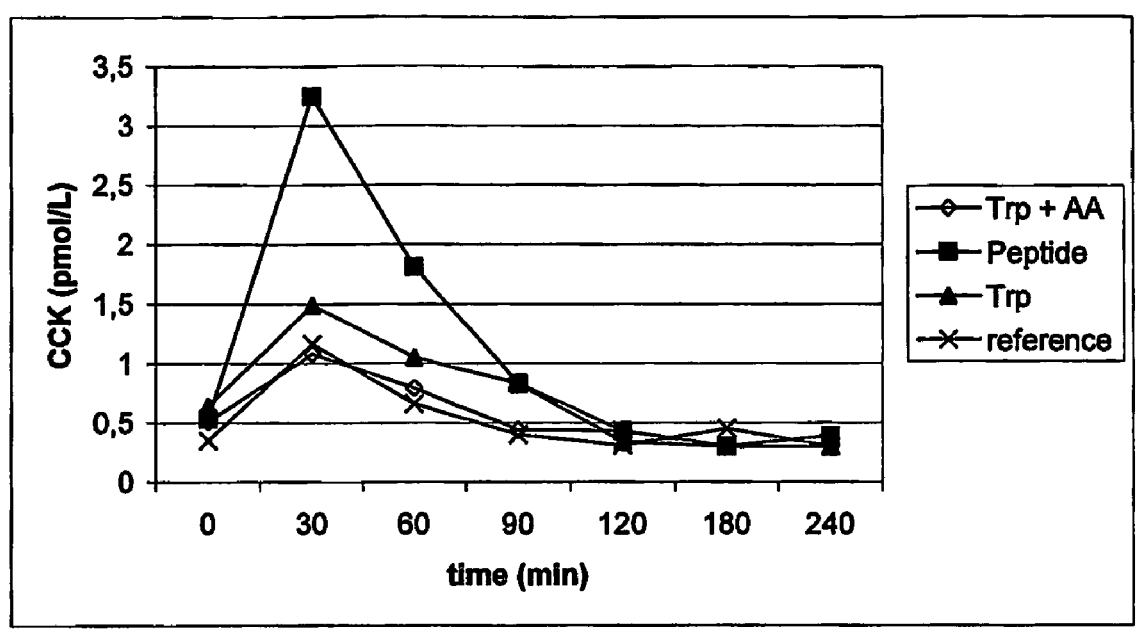

Preparation of Peptides Derived from Whey Protein Hydrolysate

A whey protein isolate solution containing 75% α-lactalbumin (Davisco) is dissolved in demenirilised water, resulting in a solution comprising 2,8 w/w % dry solids and 2 w/w % α-lactalbumin. The pH is adjusted to 2.0 using 2M phosphoric acid. Hereafter the said mixture is heated to 50° C.

The hydrolytic reaction is started by adding 0.5% E/S pepsin (Merck, USA). E/S stands for the enzyme/substrate ratio. After 6 hours the reaction is stopped by incubating the reaction for 10 minutes at 90° C. Subsequently, the pH was raised to 5.0 and the temperature was lowered to 4° C. After storage of 20 hours at this temperature, the precipitated peptides are collected by decantation and centrifugation and subsequent freeze drying.

Tryptophan is determined using a specific technique based on total enzymatic hydrolysis (Garcia, S. E.; Baxter, J. H. (1992) Determination of tryptophan content in infant formulas and medical nutrition. *J. AOAC Int.* 75:1112-1119). The amino acids phenylalanine, tyrosine, leucine, isoleucine, valine and methionine are determined according EG guideline 98/64 (3-9-1998; publication L257/14-23 of 19-9-1998). Protein (81,1%) is determined using the standard Kjeldahl method (IDF-FIL 20A, 1986). The resulting product contains 8.5% tryptophan on product, and 10.4% on peptide.

A chemical and amino acid analysis is given in table 1.

TABLE 1

| Chemical analysis (expressed on powder) | |
|---|---|
| Protein (Kjeldalh N*6.38) | 81.1% |
| Fat | 3.7% |
| Lactose | <0.1% |
| Ash (825° C.) | 4.8% |
| Amino Acid Analysis | |
| Tryptophan on powder (Trp) | 8.5% |
| Trp/protein | 10.4% |
| Trp/LNAA | 0.37 |
| (Large Neutral Amino Acids: Val, Tyr, Leu, Ile, Phe) | |
| Amino Acid Profile (per gram of protein): | |
| Alanine (Ala) | 51.4 mg |
| Arginine (Arg) | 7.3 mg |
| Aspartic acid (Asp) | 96.8 mg |
| Cystine (Cys) | 74.2 mg |
| Glutamic acid (Glu) | 155.4 mg |
| Glycine (Gly) | 14.9 mg |
| Histidine (His) | 59.9 mg |
| Isoleucine (Ile) | 25.3 mg |
| Leucine (Leu) | 131.6 mg |
| Lysine (Lys) | 109.6 mg |
| Methionine (Met) | 4.9 mg |
| Phenylalanine (Phe) | 55.4 mg |
| Proline (Pro) | 63.0 mg |
| Serine (Ser) | 47.6 mg |
| Threonine (Thr) | 77.6 mg |
| Tryptophan (Trp) | 104.3 mg |
| Tyrosine (Tyr) | 22.4 mg |
| Valine (Val) | 43.6 mg |
| Total: | 1145.2 mg |

EXAMPLE 2

Preparation of Peptides, Derived from Whey Protein Hydrolysate 2

A whey protein isolate (WPI), containing 60% α-lactalbumin (experimental product of DMV International, The Netherlands) is dissolved in an aqueous solution. The pH of the solution is adjusted using diluted phosphoric acid and heated to 45° C. Hydrolysis is started by adding 2% pepsin (Merck, 2500 FIP-U/g) and carried out for 2 hours. The reaction is stopped by pasteurising the solution at 85° C. for 10 minutes. Hereafter, the pH is raised to 5.5 and the solution is cooled to <15° C. After 10 hours, the precipitated peptides are collected using microfiltration. Typically, a membrane having a nominal molecular weight cut-off of 1 μm is used. The peptides are hereafter spray dried. The resulting product contains 9.3% tryptophan on peptide.

EXAMPLE 3

Preparation of Peptides, Derived from Whey Protein Hydrolysate 3

A whey protein solution similar to reference example 1 was hydrolysed with pepsin (American Laboratories, USA) using enzyme/substrate ratios (E/S) in w/w % of 0.25% and 0.75%. After 5 hours, the reaction was stopped by raising the pH to 5.2 using 1.0M NaOH and cooling the solution to <15° C.

The precipitated peptides were harvested after 16 hours by centrifugation.

EXAMPLE 4

Preparation of Peptides Derived from Whey Protein Hydrolysate 4

A 10% whey protein solution containing 45% α-lactalbumin (DMV International, The Netherlands) was dissolved in demineralised water. The pH was adjusted to 7.0 using 1M sodium hydroxide. Hereafter the solution was heated to 50° C.

The hydrolytic reaction was started by adding 2% ENZECO Bromelain 240 (Enzyme Development Corporation). After 21 hours the reaction was stopped by heating the solution to 85° C. for 10 minutes. Subsequently, the peptide mixture was cooled to room temperature, the pH adjusted to 4.5 using phosphoric acid and the temperature is lowered to 10° C. After storage during 12 hours at this temperature, the precipitated peptides were collected by centrifugation and subsequent freeze drying.

The resulting tryptophan content of the peptides was 8%.

EXAMPLE 5

Preparation of Peptides Derived from Whey Protein Hydrolysate 5

100 l of a 5% whey protein isolate solution (Davisco) was prepared and then hydrolysed using 2% Pepsin. The solution was hydrolysed for 12 hours at pH 3.0. The reaction was stopped by heating the solution to 80° C. for 30 minutes. Hereafter, the solution was ultrafiltrated on a pilot NF unit using Celgard NF-PES-10 membrane. The pH of the retentate was controlled at 3.0 and the solution filtered up to 200% diafiltration.

After desalting, the pH of the retentate was adjusted to 5.5 and the solution is cooled to <10° C. to facilitate precipitation of the envisaged peptides. After 10 hours of storage, the precipitate was collected using centrifugation. Hereafter, the peptides were dried.

The tryptophan and peptide concentration in the sample was 9.5% and 91%, respectively.

EXAMPLE 6

Increase of CCK Levels on Ingestion of Tryptophan Rich Peptides

The experiment described below was performed in a double-blind, four period, randomised, cross-over, placebo controlled study.

Eight healthy human volunteers were divided into four groups of two, and were refrained from any food overnight. In the morning, the test persons obtained orange juice (containing 25 g glucose) and possibly a test substance, as follows:

Group 1: orange juice containing 5,91 g peptides as obtained in example 1 per single dose orange juice (200 ml)

Group 2: orange juice containing 500 mg pure tryptophan (Ajinomoto USA, Inc.)

Group 3: orange juice containing a mix of free amino acids in the identical composition and concentration as in the juice of group 1.

The said amino acids were purchased from Ajinomoto USA, Inc.)

Group 4: orange juice without any test substance.

The experiment was repeated four times such, that all the eight volunteers eventually obtained aal the four test substances. During the four hours following the ingestion of the orange juice, blood was taken from the test persons at t=0, 30, 60 90, 120, 180 and 240 minutes after ingestion. CCK analysis was carried out using a radio-immunoassay (RIA) kit of Euro-Diagnostica (cat nr. #RB302) according to the instructions of the manufacturer.

The results are shown in table 2 below and in FIG. 1, showing a maximum CCK level of 3.25 pmol/l at t=30 minutes after ingestion. The basal level in humans is normally about 1 pmol/l and increases to between 3 and 8 pmol/l after a meal (Becker et al., Am. J. Surg., 1984 (147) pp. 124-129). As the maximum level of CCK is gradually reached between 10 and 45 minutes after ingestion of a meal (Himeno, Am. J. Gastroenterol., 1983 (78) pp. 703-707), it is very well possible that the maximum CCK level is higher than 3.25 pmol/l, and occurring between t=0 and t=30 minutes. The increasing plasma levels with 2-4 pmol are deemed to be relevant in increasing perception of satiety.

TABLE 2

| Mean CCK levels in plasma (in pmol/l, n = 8) | | | | |
|---|---|---|---|---|
| CCK (pmol/L) | amino acids | Trp-peptide | Tryptophan | Control |
| 0 minutes | 0.51 ± 0.60 | 0.53 ± 0.65 | 0.64 ± 0.78 | 0.35 ± 0.15 |
| 30 minutes | 1.08 ± 0.87 | 3.25 ± 1.48 | 1.49 ± 1.04 | 1.16 ± 1.31 |
| 60 minutes | 0.79 ± 0.86 | 1.81 ± 0.90 | 1.05 ± 1.06 | 0.66 ± 0.67 |
| 90 minutes | 0.44 ± 0.29 | 0.83 ± 0.89 | 0.83 ± 0.84 | 0.40 ± 0.18 |
| 120 minutes | 0.43 ± 0.38 | 0.43 ± 0.36 | 0.34 ± 0.11 | 0.31 ± 0.04 |
| 180 minutes | 0.30 ± 0.00 | 0.30 ± 0.00 | 0.30 ± 0.00 | 0.45 ± 0.43 |
| 240 minutes | 0.30 ± 0.00 | 0.39 ± 0.25 | 0.30 ± 0.00 | 0.30 ± 0.00 |

The invention claimed is:

1. A method for elevating the cholecystokinin level in the blood of an animal, including human, in need thereof, comprising the step of administering to said animal an effective amount of α-lactalbumin enriched whey protein hydrolysate.

2. The method according to claim 1, wherein said animal has or is at risk of developing overweight and/or obesity.

3. The method according to claim 1, wherein said hydrolysate is prepared by enzymatic cleavage of whey protein.

4. The method according to claim 3, wherein said hydrolysate is prepared by cleaving said whey protein by one or more acid proteases or cysteine proteases.

5. The method according to claim 4, wherein said acid proteases or cysteine proteases are selected from the group consisting of pepsin, papain, bromelain and a mixture of two or more thereof.

6. The method according to claim 4, wherein said whey protein is cleaved by pepsin at a pH of between 1.5-3.5.

7. The method according to claim 4, wherein said whey protein is cleaved by pepsin at a pH of between 2-3.

8. The method according to claim 1, wherein said hydrolysate is derived from whey protein isolate.

9. The method according to claim 1, wherein said hydrolysate is derived from whey protein concentrate.

10. The method according to claim 1, wherein said hydrolysate is provided as an isolate obtained by the steps of: a) providing an aqueous whey protein hydrolysate, b) controlling the pH of said aqueous whey protein hydrolysate to 4.0-6.0, c) forming a peptide precipitate, and d) isolating said precipitated peptides.

11. The method according to claim 10, wherein step a) is carried out at a temperature of below 20° C.

12. The method according to claim 1, wherein said hydrolysate is desalted.

13. A method for treating excess weight and/or obesity of an animal, including human, in need thereof, comprising the step of administering to said animal an effective amount of α-lactalbumin enriched whey protein hydrolysate.

14. The method according to claim 1, wherein said animal has an increased satiety.

15. A method for increasing satiety in an animal, including human, in need thereof, comprising the step of administering to said animal an effective amount of α-lactalbumin enriched whey protein hydrolysate.

* * * * *